(12) United States Patent
Midha et al.

(10) Patent No.: US 6,280,763 B1
(45) Date of Patent: *Aug. 28, 2001

(54) APPARATUS AND METHOD FOR TRANSDERMAL DELIVERY OF BUPROPION

(75) Inventors: Kamal K. Midha, Hamilton (BM); Hans E. Junginer, Leiden (NL); Mark Hirsh, Wellesley, MA (US)

(73) Assignee: Pierce Management, LLC, Wellesley, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/309,075

(22) Filed: May 10, 1999

(51) Int. Cl.[7] .................................................. A61F 13/02
(52) U.S. Cl. ........................ 424/448; 514/649; 514/769; 514/772
(58) Field of Search ......................... 424/448; 514/649, 514/769, 772

(56) References Cited

U.S. PATENT DOCUMENTS

| | | | |
|---|---|---|---|
| Re. 33,994 | 7/1992 | Baker et al. | 424/465 |
| 3,819,706 | 6/1974 | Mehta | 260/570.5 |
| 3,885,046 | 5/1975 | Mehta | 424/330 |
| 5,358,970 | 10/1994 | Ruff et al. | 514/649 |
| 5,427,798 | 6/1995 | Ludwig et al. | 424/464 |
| 5,541,231 | 7/1996 | Ruff et al. | 514/649 |
| 5,731,000 | 3/1998 | Ruff et al. | 424/451 |
| 5,739,136 | 4/1998 | Ellinwood, Jr. et al. | 514/252 |
| 5,753,712 | 5/1998 | Pinsker | 514/649 |
| 5,763,493 | 6/1998 | Ruff et al. | 514/617 |
| 5,834,011 | 11/1998 | Rose et al. | 424/449 |
| 5,840,327 | 11/1998 | Gale et al. | 424/448 |
| 5,843,472 | 12/1998 | Ma et al. | 424/449 |
| 5,879,701 | 3/1999 | Audet et al. | 424/448 |
| 5,906,830 | 5/1999 | Farinas et al. | 424/448 |

FOREIGN PATENT DOCUMENTS

| | | |
|---|---|---|
| WO92/21333 | 12/1992 | (WO) . |
| WO 95/03791 | 2/1995 | (WO) . |
| WO95/22324 | 8/1995 | (WO) . |
| WO96/31621 | 10/1996 | (WO) . |
| WO97/21833 | 6/1997 | (WO) . |
| WO 97/29735 | 8/1997 | (WO) . |
| WO97/35584 | 10/1997 | (WO) . |

(List continued on next page.)

OTHER PUBLICATIONS

Appel, R.A. "Clinical Efficacy and Safety of Tolterodine in the Treatment of Overactive Bladder: A Pooled Analysis", *Urology 50* (Supplement 6A) :90–96 (Dec. 1997).

Barrickman, L.L. et al. "Bupropion versus Methylphenidate in the Treatment of Attention–Deficit Hyperactivity Disorder", *J. Am. Acad. Child Adolesc. Psychiatry*, 34:5, 649–657 (1995).

Laizure, S.C. et al. "Pharmacokinetics of Bupropion and Its Major Basic Metabolites in Normal Subjects after a Single Dose", *Clin. Pharmacol. Ther.* 38:586–589 (1985).

Sweet, R.A. et al. "Pharmacokinetics of Single– and Multiple–Dose Bupropion in Elderly Patients with Drepression", *J. Clin. Pharmacol.*, 35:875–884 (1995).

*Primary Examiner*—Michael A. Williamson
(74) *Attorney, Agent, or Firm*—Herbert Dubno; Jonathan Myers (57) ABSTRACT

The invention includes an apparatus and method for transdermal delivery of bupropion base. In the method of this invention, patient is administered parenterally a bupropion base in an amount effective to alleviate withdrawal symptoms and to prevent or reduce craving of nicotine in said patient. Alternatively, an effective amount of bupropion base is delivered to alleviate depression in a patient. A transdermal delivery system includes a bupropion base. The bupropion base can be mixed with an acceptable pharmaceutical carrier.

17 Claims, 5 Drawing Sheets

FOREIGN PATENT DOCUMENTS

| | | |
|---|---|---|
| WO98/43646 | 10/1998 | (WO) . |
| WO 99/11208 | 3/1999 | (WO) . |
| WO 99/38504 | 5/1999 | (WO) . |
| WO 99/33457 | 7/1999 | (WO) . |
| WO 99/38502 * | 8/1999 | (WO) . |
| WO 99/38503 * | 8/1999 | (WO) . |

* cited by examiner

APPARATUS AND METHOD FOR TRANSDERMAL DELIVERY OF BUPROPION

BACKGROUND OF THE INVENTION

Bupropion hydrochloride is a known antidepressant sold in instant release tablet form under the brand names Wellbutkin® and Zyban®. Bupropion hydrochloride is an antidepressant of the aminoketone class and is chemically unrelated to tricyclic, tetracyclic, selective serotonin re-uptake inhibitors or other known antidepressant agents. Bupropion (BUP) hydrochloride is highly metabolized in both rats and humans. The major metabolites are the erythroamino alcohol (EB), the threoamino alcohol (TB), and the hydroxy metabolite (HB). The metabolites exhibit pharmacological activity in an antitetrabenzene model. Bupropion hydrochloride is also useful in preventing functional impairment and drowsiness seen upon administration of benzodiazepine, in the treatment of minimal brain dysfunction, tardive dyskinesia, impaired mental alertness upon ingestion of ethanol and psychosexual dysfunction. While the instant release tablets currently sold are suitable for the indicated use, there is a disadvantage to bupropion hydrochloride in that there can be an accumulation of metabolites that can be detrimental to one's health.

In a study of pharmacokinetics of bupropion hydrochloride in the elderly, six elderly patients with diagnosed depression were examined in a single and multiple dose study. Half-lives (t1/2app) of the metabolites TB, EB, and HB were 38.8+/−7.6 hours, 61.4+/−21.6 hours, and 34.2+/−4.6 hours, respectively. After multiple dosing, the half-life for bupropion and its metabolites did not change significantly, although in some patients the half-life of metabolites was substantially prolonged. In addition, there was also evidence of inordinate accumulation of metabolites. The elderly are at risk for accumulation of bupropion and its metabolites. See *J Clin. Pharmacol.* 35:876–884 (1995).

Therefore, a need exists for a new form of bupropion for delivering to the body while minimizing the formation of metabolites.

SUMMARY OF THE INVENTION

The invention includes an apparatus and method for transdermal delivery of bupropion base.

In the method of this invention, a patient is administered transdermally a bupropion base in an amount effective to alleviate withdrawal symptoms and to enhance the ability of a patient to abstain from smoking. Alternatively, an effective amount of bupropion base is delivered to alleviate depression in a patient.

A transdermal delivery system includes a bupropion base. The bupropion base can be mixed with an acceptable pharmaceutical carrier.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The present invention is directed to an apparatus and method for transdermal delivery of bupropion. A method includes administering medicament to a mammalian body, including the central nervous system, wherein a therapeutically effective amount of said medicament is transdermally administered to a mammal, preferably a human. The term "transdermal delivery" includes both transdermal (or "percutaneous") and transmucosal administration, which is delivery by passage of a drug through the skin or mucosal tissue and into the bloodstream. The term "therapeutically effective" amount means a sufficient amount of a compound to provide the desired therapeutic effect that is effective in relieving symptoms of the condition or disease being treated with minimal side effects. An "effective" amount of a permeation enhancer composition means an amount that provides a desired increase in skin permeability and, correspondingly, the desired depth of penetration, rate of administration, and amount of drug delivered.

An improvement of the present invention includes selecting a route of delivery to avoid increased formation of an unwanted and/or adverse metabolite(s), such as those produced by the gastrointestinal tract and liver when the medicaments are administered orally. In the present invention, the medicament is placed in a suitable transdermal patch formulation for dermally administering a therapeutically effective amount of the transdermal patch to bypass the gastrointestinal tract absorption and first pass metabolism in the liver and thereby to decrease the formation of the unwanted metabolites in the human body including the central nervous system. This transdermal patch is utilized over a period of one or more doses to achieve sustained high levels of the medicament.

Therapeutic dosage can be reduced via transdermal delivery. Therapeutic dosages can be reduced thereby causing reduced side effects as a result the incidence of the following side effects can be reduced or eliminated. These side effects include seizures, insomnia, agitation, psychosis, confusion, loss of appetite, weight loss, dry mouth and skin rash. Seizures are typically dose dependent and therefore there is a potential for substantially reducing the incidence of seizures. The transdermal system of delivering bupropion allows dosing of one time/day or potentially one time over a period of three days.

The pharmaceutical composition of bupropion base is in liquid or semi solid form. The transdermal patch system delivers active bupropion and therefore can reach peak therapeutic level faster with fewer or no side effects. Because the bupropion base does not enter the gastrointestinal system and forms substantially no metabolites, the precaution attending to reduced liver function may be reduced or eliminated. The transdermal delivery system allows steady state delivery, reduce large fluctuation of bupropion in the blood, and allow the peak plasma levels to be achieved quicker.

For smoking cessation and depression, the transdermal system offers a more effective delivery system as the patient does not have to remember to take the oral tablet at specified times. Patients who have reduced hepatic functions or other liver disease because of chronic intake of alcohol are at a reduced risk from using bupropion in the delivery system. Individuals who have a reduced renal function are not prevented from using bupropion because there are negligible amounts of metabolites produced. The incidence of seizures can be reduced because seizures are dose dependent and it can be anticipated that a lower dose of bupropion is necessary as the transdermal system allows the bupropion to enter the blood without passing through the gastrointestinal system and liver.

In one embodiment, the transdermal system contains bupropion base as well as isomers (+) and (−) in equal amounts in acrylic-based polymer pressure sensitive adhesives with a resinous cross-linking agent (either based on silicone polymers or polyacrylates and alcohol) to provide a continuous source of active ingredients. Each unit is sealed in a paper polyethylene-foil pouch. Isomers of bupropion can be separated by known methods. Stabilizers in the reservoir of the patch include DL Tocopheral solution in alcohol, butylated hydroxy anisole, vitamin E succinate, l-ascorbic plamitate and other known stabilizers. Examples of suitable transdermal delivery systems for bupropion base include systems disclosed in U.S. Pat. Nos. 5,834,011, 5,840,327 and 5,879,701. The teachings of each patent are incorporated by reference herein.

Figure 1:
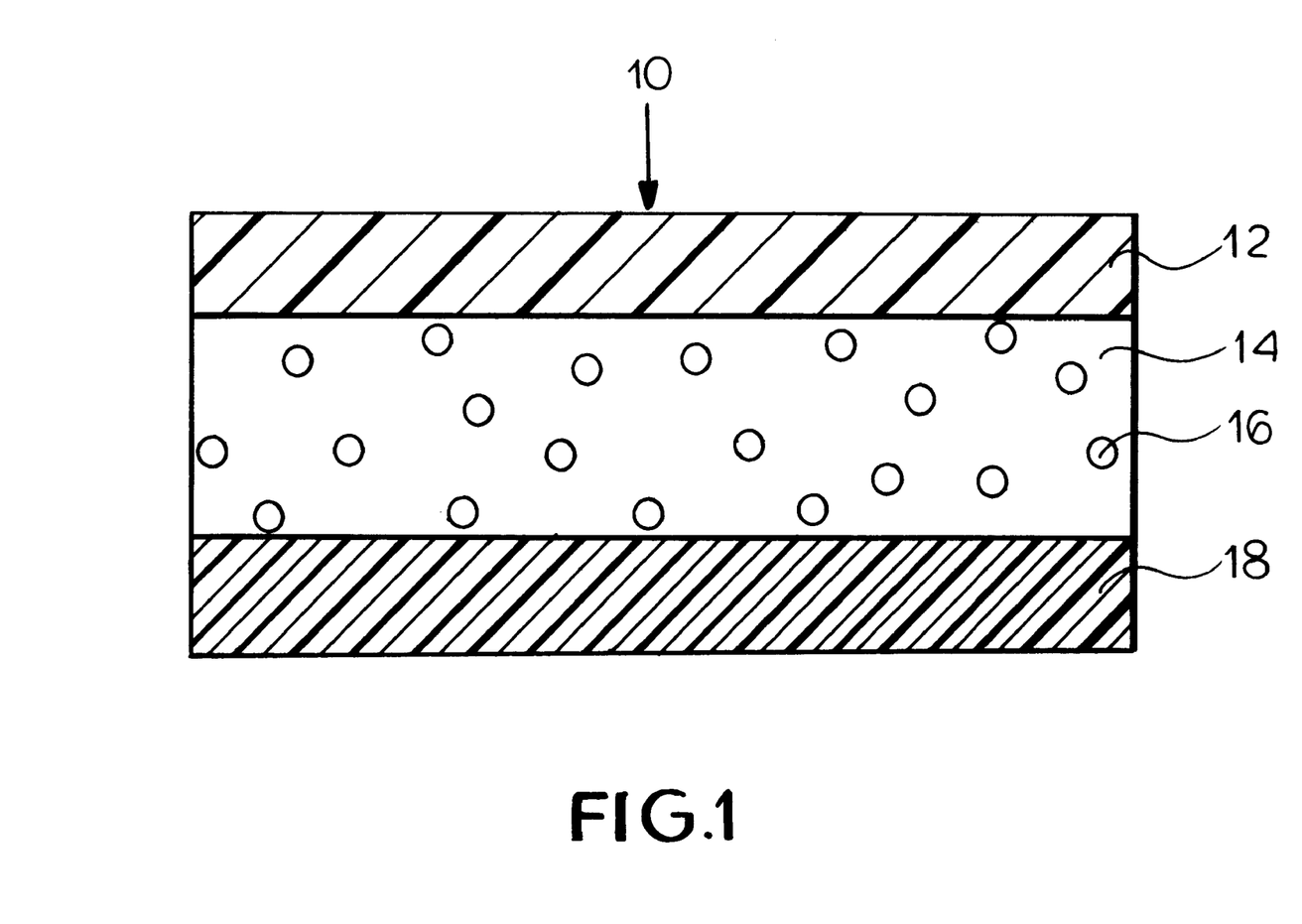
FIG. 1 shows a schematic illustration of a transdermal delivery system for use with the present invention.

Reservoir layer 14 in FIG. 1 is a means for containing the drug and an adhesive for securing the device to the skin during use. As release liner 18 is removed prior to application of the device to the skin, reservoir layer 14 serves as the basal surface of the device which adheres to the skin. Reservoir layer 14 includes a pressure-sensitive adhesive suitable for long-term skin contact. Reservoir layer 14 is physically and chemically compatible with bupropion and the carriers and vehicles employed.

"Carriers" or "vehicles" refer to carrier materials suitable for transdermal drug administration and include any such materials known in the art, such as any liquid, gel solvent, liquid diluent, solubilizer, or the like, which is nontoxic and which does not interact with other components of the composition in a deleterious manner. Examples of suitable carriers for use herein include water, silicone, liquid sugars, waxes, petroleum jelly, and a variety of other materials. The term "carrier" or "vehicle" can also refer to stabilizers, crystallization inhibitors, or other types of additives useful for facilitating transdermal drug delivery. Suitable materials for this layer include, for example, polysiloxanes, polyisobutylenes, polyurethanes, plasticized ethylenevinyl acetate copolymers, low molecular weight polyether amide block polymers (e.g., PEBAX), tacky rubbers, such as polyisobutene, polystyrene-isoprene copolymers, polystyrene-butadiene copolymers, and mixtures thereof. Presently preferred adhesive materials for use as reservoir layer 14 are polyisobutylenes, silicones and polyurethanes, with polyisobutylenes particularly preferred.

In a preferred embodiment, the reservoir matrix includes a dispersing agent which aids in maintaining the particulate phase dispersed in the continuous phase. In other embodiments, nonionic excipients, such as lauric acid, propylene glycol monolaurate, myristyl lactate, lauryl lactate, or the like, facilitate dispersion.

The cold flow properties of the polymer adhesives of the bupropion delivery system are considered acceptable when adhesion of the transdermal patch to the skin of the user remains high throughout the drug delivery period and the adhesive does not extend beyond the boundary of the patch.

Release liner 18 is a disposable element which protects the device prior to application. Typically, the release liner 18 is formed from a material impermeable to the drug, vehicle and adhesive, and which is easily stripped from the contact adhesive. Release liners are typically treated with silicone of fluorocarbons. Silicone-coated polyester is a preferred embodiment.

One type of drug delivery system for transdermally administering bupropion is shown in FIG. 1. System 10 is in the form of a laminated composite having a backing layer 12, a reservoir layer 14 containing the drug 16 either dispersed therein, or adsorbed or absorbed by a particulate hydrophilic material, and a release liner 18.

The backing layer 12 functions as the primary structural element of the device and provides the device with much of its flexibility, drape and, preferably, occlusivity. The material used for the backing layer should be inert and incapable of absorbing drug, enhancer or other components of the pharmaceutical composition contained within the device. The backing is preferably made of one or more sheets or films of a flexible material that serves as a protective covering to prevent loss of drug or vehicle or both by transmission through the upper surface of the device, and imparts a degree of occlusivity to the device, such that the area of the skin covered on application becomes hydrated. The material used for the backing layer should permit the device to follow the contours of the skin and be worn comfortably on areas of skin, such as at joints or other points of flexure, that are normally subjected to mechanical strain with little or no likelihood of the device disengaging from the skin due to differences in the flexibility or resiliency of the skin and the device. Examples of materials useful for the backing layer are polyesters, polyethylene, polypropylene, polyurethanes and polyether amides. The layer is preferably in the range of about 15 micrometers to about 250 micrometers in thickness.

The bupropion transdermal infusion system is a flat unit designed to provide continuous controlled release of bupropion base or its isomers through the intact skin. The rate of release of bupropion base or its isomers is linearly dependent upon the area of the applied system; each square cm of the applied system delivers approximately 2 mg to 7.5 mg/cm$^2$. The patch size ranges from about five to forty square centimeters. The rate of delivery of the bupropion from a forty square centimeter patch ranges from about 40 mg/day to 300 mg/day.

Bupropion hydrochloride is commercially available under the name Wellbatrin and Wellbutrin from Burrough Wellcome. For bupropion (1-(3-chlorophenyl-Z-[(1,1-dimethylethyl) amino]-1-propanone, its preparation is described in U.S. Pat. Nos. 3,819,706 and 3,885,046, wherein the teachings of each patent are incorporated by reference.

Preparation of bupropion base can be prepared by a suitable method. In one embodiment, 1.2 g bupropion HCl is dissolved in 20 ml of distilled water to which 0.1 N NaOH is added until the pH is about 12. Then this mixture is extracted with 50 ml of diethylether by shaking followed by centrifugation. The ether phase containing the bupropion base is separated and the remaining watery phase is treated three times with 80 ml diethylether. The unified ether phases are dried (removal of residual water) by adding 15 g anhydrous $K_2CO_3$, filtrated and the ether is evaporated at 50° C. under vacuum (rotavapor). The residual phase (bupropion base) (1.0 g) is dissolved in 6 ml propylene glycol and stored until further use under nitrogen gas in a tight bottle in the dark. Bupropion base can be prepared by other procedures that are known in the art.

In humans, bupropion metabolism occurs via the reduction of its carbonyl group and/or the hydroxylation of its tertiary butyl group. According to the U.S. Food and Drug Administrations' Summary Basis of Approval (SBA), nine metabolites have been identified in urine, four of which have shown activity in mice. These are erythro amino alcohol, threo amino alcohol, erythro amino diol, and morpholindolmetabolite, which is formed from the hydroxylation of the t-butyl group.

Bupropion undergoes a very rapid first pass metabolism. Absolute bioavailability is generally not determinable in humans because of the lack of availability of an intravenous dosage form. In rats and dogs, the absolute bioavailability is in the range of about five to twenty percent bioavailable.

Following oral dosage, drug blood concentration is dose proportional from 100 to 250 mgs. 'C' max occurs in approximately 2 hours, and its biological half life is approximately 14 hours (range 8–24 hours). Following oral administration of radio labeled carbon 14 bupropion, 87% of the radioactivity is recovered in the urine and 10% in the feces. As expected from the extensive first pass metabolism, less than 0.5% is excreted unchanged. Bupropion is 80% bound to albumin and its (single) oral dose kinetics is best described by a 2 compartment open model with first order absorption.

The morpholindometabolite (M) is half as potent (antidepressive effect) as parent medicament and appears in the systemic circulation almost as fast, following the administration of a single oral dose. The MM 'C' max is three times and its AUC is fifteen times, that of medicament drug. Its biological half-life $t_{1/2}$=24 hours. The threo amino alcohol metabolite (TAM) is also half as parent medicament (antidepressive effect), and its kinetics parallel that of MM. The erythro amino alcohol and erythro amino diol metabolites are not quantifiable after a 100 mg, single, oral dose.

According to the SBA, studies in mouse, rat, and dog, show that bupropion induces its own metabolism. The mouse shows a 58% reduction over ten days, and the dog, 76 and 90% reductions at two different dose levels over one year of treatment. Metabolites have half-lives exceeding that of parent drugs, with resultant significant metabolite accumulation after administration of multiple doses.

EXAMPLES

Flux Studies Using Full Thickness Human Skin
Preparation of Human Stratum Corneum Samples Human abdominal skin obtained by surgical operation was processed immediately upon arrival on the day of the surgery. After the removal of subcutaneous fact, the skin was dermatomed using an electric dermatome (Padgett Dermatome, Kansas City, USA) to a thickness of approximately 250 $\mu$m. The sheets were used the same days as obtained for diffusion experiments. Until use the sheets were kept dermal side down in a Petri humidity disk.

Formulation of the Donor Solutions

For standardization, saturated solutions of bupropion in propylene glycol were made and 80% of the saturated solution was used as donor solutions. 1,100 mg bupropion has been suspended in 6.0 ml propylene glycol and was vortexed at 90 rpm for 68 hrs at 32° C. in a thermostated shaking cupboard. Controls have been done every 24 hrs to assure that sufficient undissolved drug was in the vessel. Thereafter the suspension was centrifuged (3,000 rpm) for 10 minutes and the clear supernatant was used as saturated solution.

For the diffusion experiments the donor solutions were freshly prepared for each experiment, 550 mg of the bupropion base were suspended in 3.0 ml propylene glycol (PG) and treated as previously described. To the saturated supernatant, PG was added to result in a 80% saturated solution, from which the drug content was analyzed (104 mg/ml PG).

Formulation of the Acceptor Solution

Phosphate buffered saline (PBS) was used as acceptor solution and was freshly made and degassed with a vacuum pump before each experiment. PBS buffer solution pH 7.4 had the following composition: NaCl, 8 g/l; $Na_2HPO_4 2H_2O$, 1.4 g/l; ECl, 0.2 g/l, $KH_2PO_4$, 0.2 g/l; NaN, 1.0 g/l and 5 ml Streptomycin/penicillin solution (5,000 units in 0.9% NaCl).

Transdermal Permeation Studies

Figure 2:
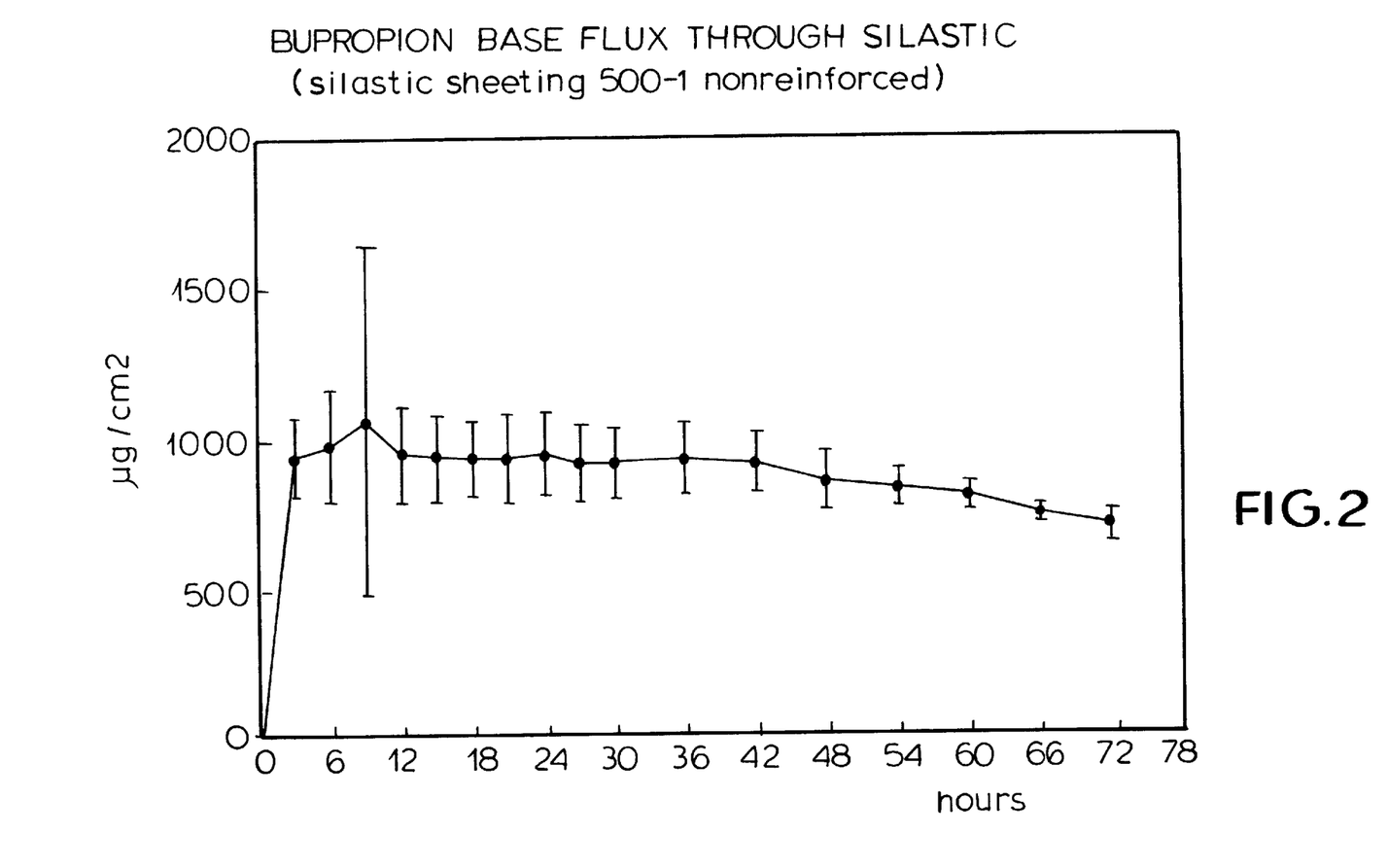
FIG. 2 shows the results of flux by bupropion base across silastic sheeting.
Figure 3:
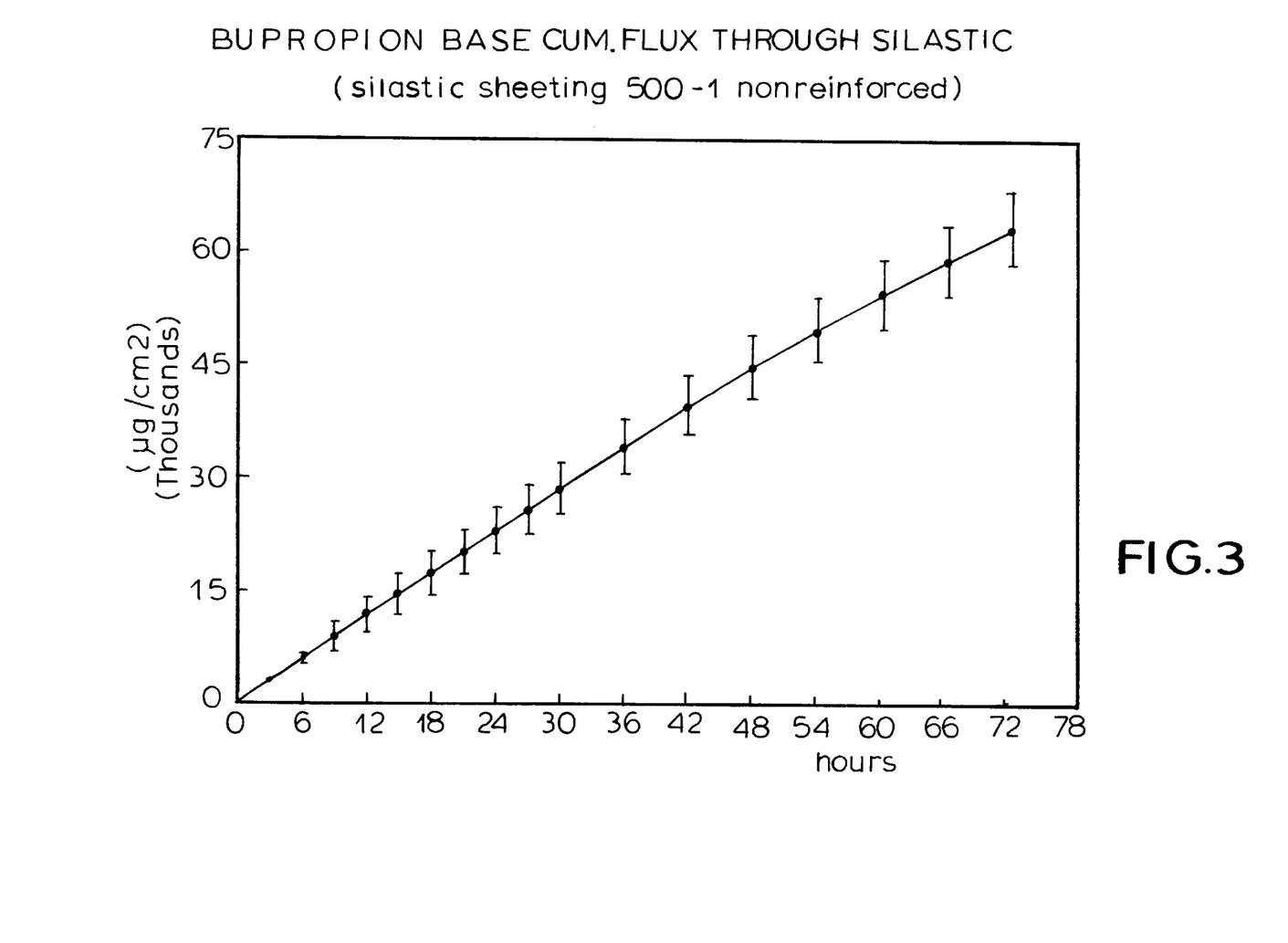
FIG. 3 shows the results of the cumulative flux by bupropion base across silastic sheeting.
Figure 4:
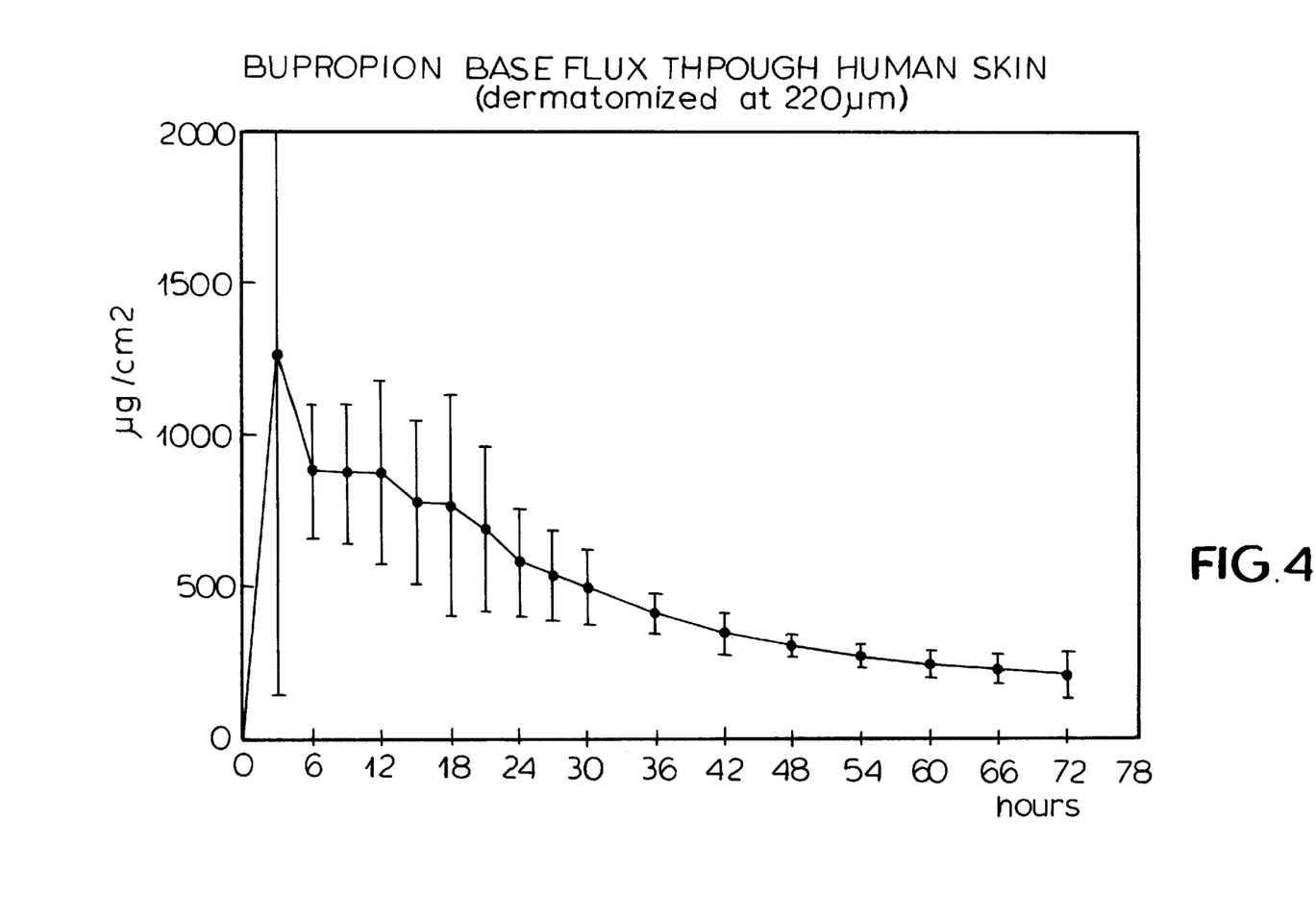
FIG. 4 shows the results of flux by bupropion base through human skin dermatomized at 220 micrometers.
Figure 5:
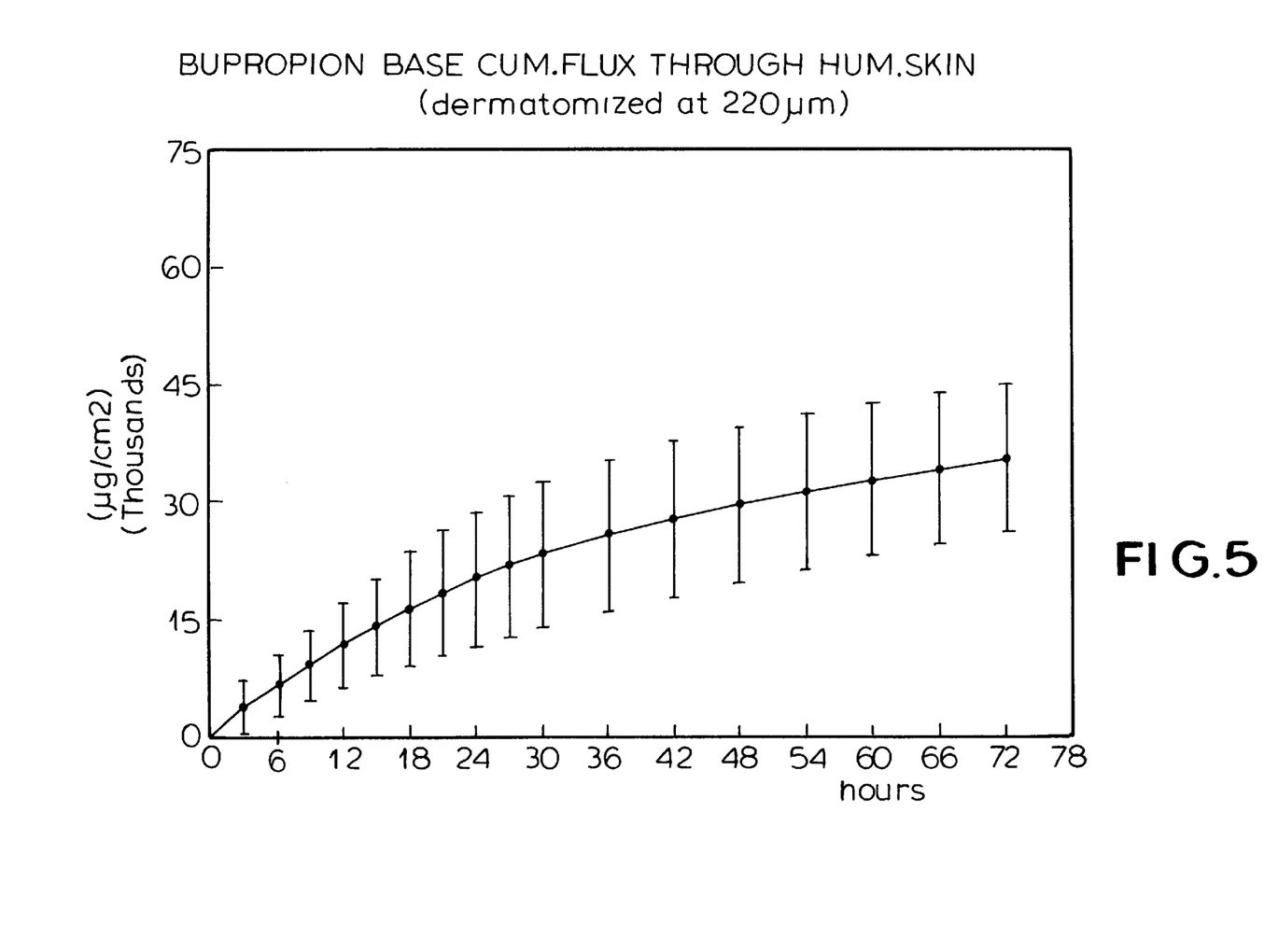
FIG. 5 shows the results of cumulative flux by bupropion base through human skin dermatomized at 220 micrometers.

Transdermal permeation studies with bupropion across human stratum corneum or dermatomized skin were performed as follows: The diffusion cells used have been described by Tanojo et al (J. Control. Rel. 45 (1997) 41–47). To use academic solutions, the original donor part of the described cell design has been modified in such a way that the spiral has been replaced by a donor chamber of 700 $\mu$l volume. To assure complete contact of the skin membrane adduct with the spiral of the acceptor phase, a slight pressure of the donor phase to the membrane adduct was achieved by closing the donor chamber with a moveable disk connected with a spring to exert the pressure. Pieces of 18 mm diameter of dermatomized skin have been punched and used. To prevent the dermatomized skin from further hydration in the diffusion experiments with bupropion the sheets were sandwiched between two silastic sheetings (500-1, non-reinforced, Dow Corning, USA) with the both sides fixed with medical adhesive (Dow Corning, USA). FIG. 2 shows the results of flux by bupropion base across silastic sheeting. FIG. 3 shows the results of the cumulative flux by bupropion base across silastic sheeting. The sandwiched dermatomized skin sheets have been mounted between the two parts of the diffusion cell. The diffusion area was 55.2 square millimeters. The acceptor phase was pumped through the spiral of the acceptor chamber with a rate of 5 ml/hr (Ismatec, Dijkstra, Lelystad, The Netherlands). During the experiments, the diffusion cells were placed in a water bath thermostated at 32° C. Samples were taken every 3 hrs until the end of the experiments (72 brs) and sampled by a fraction collector (Retriever III, Beun de Ronde, Abcoude, The Netherlands). FIG. 4 shows the results of flux by bupropion base through human skin dermatomized at 220 micrometeres. FIG. 5 shows the results of cumulative flux by bupropion base through human skin dermatomized at 220 micrometers.

HPLC Analysis

A spectroflow 400 pump (Separations, Hendrik Ido Ambacht, The Netherlands) was used to deliver the mobile phase, consisting of acetronitrile 0.1 m $KF_2PO_4$ pH3 20:80 (v/v) with a flow rate of 0.8 ml/min. The mobile phase was degassed with a vacuum pump and chromatography was performed at ambient temperature. Sample amounts of 20 $\mu$l were injected with a Gilson model 321 autosampler (Gilson Middleton, Wisconsin USA) with a 20 microliter loop built in onto a inertsil 5 ODS column (Chrompack Nederland BV, Bergen op Zoom, The Netherlands). This analytical column was proceeded by a chromspher 5C18 guard column (Chrompack). Bupropion base was detected by UV absorption at 310 nm using a spectra 100 spectrophometer (Spectra-Physics, Breda, The Netherlands). Chromatogram 5 were integrated by WOW integrated computer program.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A transdermal delivery system consisting essentially of a bupropion base in a therapeutically acceptable amount.

2. The transdermal delivery system of claim 1 wherein said bupropion base is mixed with an acceptable pharmaceutical carrier.

3. The transdermal delivery system of claim 2 wherein said bupropion base is a racemic mixture of the bupropion isomers.

4. The transdermal delivery system of claim 2 wherein said bupropion base is a bupropion base (+) isomer.

5. The transdermal delivery system of claim 2 wherein said bupropion base is a bupropion base (−) isomer.

6. The transdermal delivery system of claim 2 wherein said system delivers about 2 to 7.5 mg/cm$^2$ of bupropion and/or its isomers.

7. The transdermal delivery system of claim 2 wherein said system delivers about 40 to 300 mg/day of bupropion base via a system having an area in the range of between about five to forty square centimeters.

8. The transdermal delivery system of claim 1 wherein said bupropion base includes an effective amount to alleviate withdrawal symptoms of nicotine in a patient.

9. The transdermal delivery system of claim 1 wherein said bupropion base includes an effective amount to alleviate depression in a patient.

10. A method for treating withdrawal symptoms and preventing or reducing craving for nicotine in a patient, comprising:

administering transdermally to a patient a composition consisting essentially of a bupropion base in an amount effective to alleviate withdrawal symptoms and to prevent or reduce craving of nicotine in said patient.

11. The method of claim 10 wherein said bupropion base is administered in an amount of between about 40 and 300 mg/day via a transdermal patch.

12. The method of claim 10 wherein said bupropion base is administered in an amount of between about 40 to 300 mg/day of bupropion base via a system having an area in the range of between about five to forty square centimeters.

13. A composition for use in the method of claim 10 consisting essentially of a bupropion base and an acceptable pharmaceutical carrier, wherein the bupropion base is in an amount effective to alleviate withdrawal symptoms and prevent or reduce craving of nicotine in a patient.

14. A method for alleviating depression in a patient, comprising:

administering transdermally to a patient a, a composition consisting essentially of a bupropion base in an amount effective to alleviate depression in a patient.

15. The method of claim 14 wherein said bupropion base is administered in an amount of between about 40 and 300 mg/day via a transdermal patch.

16. The method of claim 14 wherein said bupropion base is administered in an amount of between about 40 to 300 mg/day of bupropion base via a system having an area in the range of between about five to forty square centimeters.

17. A composition for use in the method of claim 14 consisting essentially of a bupropion base and an acceptable pharmaceutical carrier, wherein the bupropion base is in an amount effective to alleviate depression in a patient.

* * * * *